(12) United States Patent
Watson (10) Patent No.: US 6,648,862 B2
(45) Date of Patent: Nov. 18, 2003

(54) PERSONALLY PORTABLE VACUUM DESICCATOR

(75) Inventor: Richard Watson, Mc Pherson, KS (US)

(73) Assignee: Spheric Products, Ltd., San Antonio, TX (US)

( * ) Notice: Subject to any disclaimer, the term of this patent is extended or adjusted under 35 U.S.C. 154(b) by 39 days.

(21) Appl. No.: 09/996,970

(22) Filed: Nov. 20, 2001

(65) Prior Publication Data
US 2003/0097100 A1 May 22, 2003

(51) Int. Cl.[7] .................................................. A61M 1/00
(52) U.S. Cl. ........................................ 604/319; 604/327
(58) Field of Search ................................ 604/317–328, 604/313

(56) References Cited

U.S. PATENT DOCUMENTS

| | | | |
|---|---|---|---|
| 4,710,165 A | | 12/1987 | McNeil et al. |
| 4,930,997 A | | 6/1990 | Bennett |
| 5,002,541 A | * | 3/1991 | Conkling et al. ........... 604/319 |
| 5,073,172 A | | 12/1991 | Fell |
| 5,134,994 A | | 8/1992 | Say |
| 5,419,769 A | * | 5/1995 | Devlin et al. ............... 604/119 |
| 5,429,601 A | * | 7/1995 | Conley et al. ............... 604/65 |
| 5,449,347 A | * | 9/1995 | Preen et al. ................ 604/118 |
| 5,466,229 A | * | 11/1995 | Elson et al. ................ 604/317 |
| 5,522,808 A | * | 6/1996 | Skalla ........................ 604/319 |
| 5,634,893 A | * | 6/1997 | Rishton ...................... 604/6.1 |
| 5,944,703 A | | 8/1999 | Dixon et al. |
| 6,024,731 A | | 2/2000 | Seddon et al. |
| 6,142,982 A | | 11/2000 | Hunt et al. |
| 6,152,902 A | | 11/2000 | Christian et al. |
| 6,210,360 B1 | * | 4/2001 | Kong ........................... 604/73 |
| 6,352,525 B1 | * | 3/2002 | Wakabayashi .............. 604/322 |
| 6,503,450 B1 | * | 1/2003 | Afzal et al. .................... 422/45 |

OTHER PUBLICATIONS

Ametek Product Bulletin, Lamb Electric, Mar., 1998.*

* cited by examiner

Primary Examiner—Weilun Lo
Assistant Examiner—Michael Bogart
(74) Attorney, Agent, or Firm—Loeffler Jonas & Tuggey LLP (57) ABSTRACT

The vacuum desiccator low pressure vacuum pump and trap and is transportable upon a user's person. The device is especially useful to remove excess fluids from wounds and incisions as they heal. The device includes a desiccator cartridge containing a fluid trapping agent. The desiccator cartridge is connected to a vacuum pump member providing a low vacuum pressure to the interior chamber of the desiccator cartridge. A small battery powered, electric motor drives the pump member. An electrical control circuit, including the battery power source, controls the operation of the electric motor. A single passage, one-way, gas/liquid flow pathway connects the inlet port of the desiccator cartridge to an occlusive dressing covering the wound to be drained. The control circuit includes one or more ancillary circuits for controlling operation of the device, such as: a power circuit, a moisture sensor, a timer circuit, a vacuum pressure sensor, and a pressure differential sensor.

34 Claims, 4 Drawing Sheets

PERSONALLY PORTABLE VACUUM DESICCATOR

FIELD OF THE INVENTION

The present invention is in the field of portable, motor driven vacuum p-umps having a movable working member which is motivated by electricity or a magnetic field. More specifically, the present invention relates to a personally portable, low negative pressure, motor driven vacuum pump having an electric power storage means and a moisture trap.

BACKGROUND OF THE INVENTION

A number of portable, low pressure vacuum apparatuses capable of producing vacuum pressures down to about 500 mm HG currently exist. Medicine, particularly the wound healing arts, is a field where such devices have a specific utility. In the wound healing arts, it has been recognized that the removal of excess fluid from a wound site can improve the healing of the wound. This recognition has motivated the field to develop wound treatment regimens that include the use of vacuum devices for removing excess exudate from a wound site. For example, in full thickness dermal wounds devices to assist in the removal of excess fluid from these wounds have been developed and used. Further, because of the recognized benefits of encouraging patients to be active and mobile if possible, these devices need to be portable, and preferably, personally portable.

One strategy for providing a personally portable, low pressure vacuum source for drainage of wound site involves the use of a passive vacuum reservoir. Examples of this types of device includes those disclosed by Fell, U.S. Pat. No. 5,073,172; Seddon et al., U.S. Pat. No. 6,024,7311 and Dixon et al., U.S. Pat. No. 5,944,703. Typically, these devices comprise an evacuated cannister attached to a drainage tube. Because the vacuum pressure in the reservoir of these devices continuously decreases as the wound is drained (and the reservoir filled), they often include a means for regulating the pressure delivered to the wound site at some level below the maximum pressure of the vacuum reservoir. Additionally, these devices require a reservoir of a relatively larger volume than that of the volume of fluid they are capable of removing from a wound site.

Recognizing these limitations, the field has been further motivated to develop means for providing a portable, low pressure vacuum source for drainage of a user's wound site which provides a relatively constant vacuum pressure. A strategy for accomplishing this objective includes having the device comprise a vacuum pump to provide a constant low pressure vacuum source, or to replenish a separate vacuum reservoir. An example of this type of device includes that disclosed by McNeil et al., U.S. Pat. No. 4,710,165. Also see U.S. Pat. No. 5,134,994 to Say. Although portable, these devices are bulky and obvious to an observer of the user, and may subject the user to embarrassment or personal questions. It would be beneficial to have a portable vacuum device that was personally portable by the user without being obvious to an observer.

An apparatus which addresses this latter benefit is disclosed in U.S. Pat. No. 6,142,892 to Hunt et al. The Hunt apparatus is supported on a belt or harness worn by the user, and is small enough to be unobtrusive when worn under a jacket or the like. However, the Hunt apparatus utilizes a liquid reservoir containing the fluids drained from a wound site. Fluids contained in the liquid reservoir of Hunt are subject to slouching, which may adversely affect the function of the Hunt apparatus if the fluid prematurely enters an inappropriate pathway (the outlet end of the cannister). Also, the Hunt device requires multiple tubes or a multi-lumen tube running from the device to the wound site to accomplish its full utility. Additionally, the Hunt apparatus is intended to be worn by a patient at waist level or higher. This means that wound sites below and distal to the users waist can be subjected to a higher vacuum pressure than with a device that may be located more proximal the wound site than the Hunt apparatus.

Although the above apparatuses may be useful in the field for accomplishing their intended purposes, it would be beneficial to have an alternative personally portable vacuum device that can be worn unobtrusively by the user, and which is not subject to slouching of the fluid it retains, and further which does not require special tubing to connect it to a wound site.

SUMMARY OF THE INVENTION

The present desiccator is a personally portable vacuum pump and moisture trapping device. The invention is useful where a user desires to carry a device for collecting and trapping small volumes of liquids. As a specific example, the present invention is therapeutically useful to provide a personally portable low negative pressure source and trap for aspirating and collecting fluid exudate from a wound or incision. A further benefit of the present invention for such applications involving biological waste is that the trap and all other components of the desiccator device that contact the aspirated biological materials are removable from the device and are replaceable. The desiccator device includes a trap, a vacuum pump head member, an electric motive mechanism and an electric control and power circuit.

The trap comprises a desiccator cartridge enclosing an interior space or chamber. An inlet port and an outlet port provide gas/liquid flow communication with the interior chamber of the desiccator cartridge. The desiccator cartridge is of a design and construction to withstand the application of an appropriate vacuum without substantial collapse of the interior chamber. Some distortion of the cartridge while under vacuum is desirable in some applications, e.g., where buffering of the vacuum pressure of the system is beneficial. A trapping agent is contained within the interior chamber for retaining the fluid that enter the chamber. The composition of the trapping agent is selectable by one of ordinary skill in the art in view of the teaching herein and in consideration of the characteristics of the fluid to be trapped.

A vacuum pump member or pump head is connected in gas flow communication with the interior chamber of the trap by having the low pressure port of the vacuum pump member being connected to the outlet port of the trap. The exhaust port of the vacuum pump member is vented to atmosphere. Operation of the vacuum pump member develops a low vacuum pressure which is communicated to the interior chamber of the desiccator cartridge and then to the inlet port of the trap. The vacuum pressure at the inlet port of the trap is selectable by the ordinary skilled artisan depending on the intended use of the present device. Typically, the selected vacuum pressures range less than about 250 mm Hg, and in part depends on the vacuum pressure to be delivered to the wound site and the any loss of vacuum pressure across the delivery tube connecting the inlet port to the wound site. An electric motive means (an electric motor) is coupled to the vacuum pump member and drives the pump head. An electrical control circuit, including an electrical power source, is in electrical communication with the electric motive means. The control circuit is operable to control the operation of the electric motive means.

The desiccator cartridge of the trap has only a single, ingress gas/liquid flow pathway, which is the inlet port. Additionally, the flow path at the inlet port is unidirectional, in that gas/liquid flow can enter the trap via the inlet port, but not exit or back flow out of the trap via the inlet port. Optionally, the personally portable vacuum desiccator includes a single passage gas/liquid flow path delivery tube for connecting the trap to a source of gas or liquids to be delivered into the trap. The delivery tube has an input end for communicating with the gas/liquid source and an output end connectable to the inlet port of the desiccator cartridge. A one-way valve is located proximate the inlet port of the desiccator cartridge. The one-way valve prevents the contents of the desiccator cartridge from back-flowing out of the inlet port. The one way valve may be separate from or incorporated into the inlet port. The desiccator cartridge is removable from the vacuum desiccator and separately disposable. A fresh desiccator cartridge is installed in the desiccator to replace the removed cartridge.

The desiccator cartridge contains a trapping agent for containing the liquids or moisture delivered to the trap under the force of the vacuum. The trapping agent combines with the liquid or moisture to alter its physical features, i.e., from a liquid or vapor to a mixed phase or solid state. Compositions suitable for use as trapping agents in the present invention are selectable by one of ordinary skill in the art in view of the present disclosure and teachings herein. The trapping agent should adsorb, absorb or in some way combine with the liquid or moisture to immobilize and keep it from sloshing in the desiccator cartridge as it is accumulated in the interior chamber. Examples of potentially suitable trapping agents include: a desiccant, an adsorbent and an absorbent. Specific examples include silica gel, sodium polyacrylate, potassium polyacrylamide and related compounds. Such moisture trapping materials are often found in disposable baby diapers and in feminine napkins. The level of moisture in the desiccant chamber is monitored by the moisture sensor circuit. When the amount of moisture trapped in desiccant material approaches saturation, the chamber may either be removed and disposed of or recharged with fresh desiccant material and repositioned in the device (depending on the design of the desiccator cartridge).

The present vacuum desiccator can further comprise a filter for blocking bacteria and/or untrapped moisture from passing into the vacuum pump member or from being vented to atmosphere. The filter may be located proximate the outlet port to protect the pump member and/or proximate the exhaust port to prevent venting bacteria or moisture to atmosphere.

The electric motive means of the vacuum desiccator includes an electric motor. The motor is coupled to the vacuum pump member to drive the pump. The motor may be coupled to the pump head by any of a number of means known to and practicable by the ordinary skilled artisan. For example, the motor shaft may be integrated with the vacuum pump head, it may be mechanically coupled to the vacuum pump so as to be readily separable from the pump head, or it may be magnetically coupled to the pump head so as to, again, be readily separable from the vacuum pump member. A readily separable motive means is particularly useful where the vacuum pump member and the desiccator cartridge are integrated together as a unit.

A purpose of the electrical control circuit is to monitor the condition of the device and to control operation of the motive means. The electrical control circuit includes the electrical power source for the device. The power source comprises an electrical power storage means, such as a battery. A feature of the power source is that the electrical storage means is removable from the electrical control circuit and is replaceable. Additionally, the electric control circuit optionally includes other ancillary circuits for the operation and control of the device. These circuits include: a moisture sensor circuit for detecting the presence of moisture proximate the low pressure port of the vacuum pump member; a timer circuit for intermittently operating the electric motive means; a vacuum pressure sensor circuit for detecting a vacuum pressure in the interior chamber or elsewhere in the device; and a pressure differential sensor circuit for sensing a difference in pressure between the inlet and outlet ports of the desiccator cartridge.

The component parts of the vacuum desiccator device which are in gas/liquid flow communication are replaceable. This allows the components of the device which are exposed to contact with the wound fluids to be separable from the other components of the device to facilitate cleaning or disposal of contaminated components.

The present personally portable vacuum desiccator can further comprise a housing for containing some or all of the component parts of the device. For example, the housing may contain the electric motive means and the electrical control circuit, while the other components are simply attached to the housing, e.g., an integrated pump head/trap combination assembly. Other configurations obviously are possible, such as a housing containing the electric motive means and the electrical control circuit and additionally either or both of the trap (desiccator cartridge) and the vacuum pump member.

Additionally, the present vacuum desiccator device may comprise the battery being housed in a battery compartment attached or integral to the desiccator cartridge of the moisture trap. In this configuration, the battery and the desiccator cartridge are replaceable in the device as a single unit.

It is a feature of the present invention that the personally portable vacuum desiccator can be used as part of a treatment regimen to promote wound healing by drawing excess wound exudate away from the wound site. As an example of using the desiccator for this purpose, an open, full thickness dermal wound is covered with an air tight dressing, such as are commercially available. The input end of the gas/liquid flow delivery tube is positioned under the dressing in flow communication with the wound site. The vacuum desiccator is activated, a low negative pressure is produced at the wound site via the delivery tube and excess fluids excreted by the wound are removed under the force of the low negative pressure.

DETAILED DESCRIPTION OF THE INVENTION

The personally portable vacuum desiccator is a device useful as a source for providing a low vacuum pressure for removing excess wound exudate from dressed dermal wounds. This application of present personally portable vacuum desiccator is useful for promoting wound healing by draining such excess wound exudate from the wound site.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1:
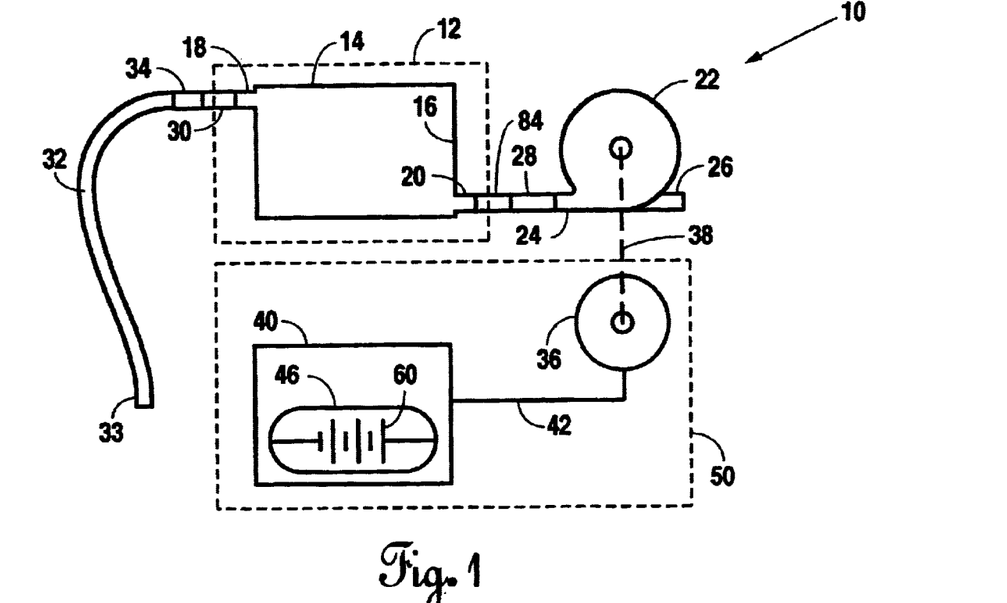
FIG. 1 is a schematic diagram of the major components of the present vacuum desiccator showing the electric control circuit contained in a housing with the motor coupled to the trap and vacuum pump member.
Figure 2A:
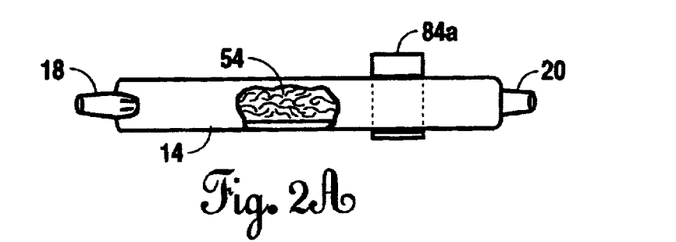
FIG. 2A is a side elevation and partial cross-sectional view of the desiccator cartridge of the present device, showing the interior chamber containing a trapping agent.
Figure 2B:
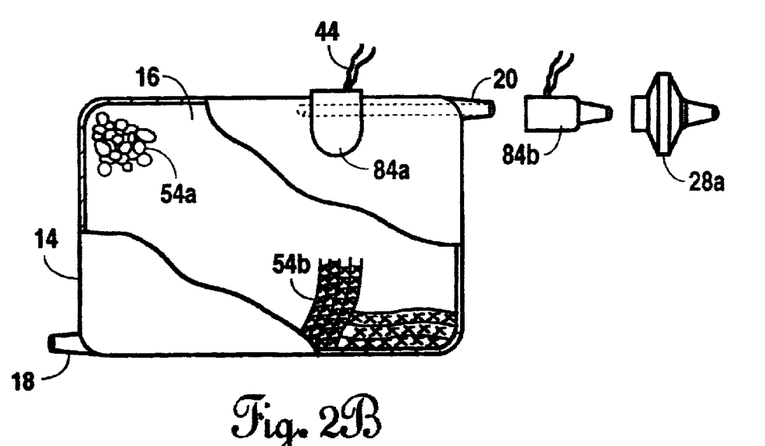
FIG. 2B is a top plan and partial cross-section view of the desiccator cartridge showing the interior chamber containing alternative trapping agents and showing alternative moisture/fluid sensors for detecting fluid in flow path proximate the outlet port of the cartridge. Also shown is a separately mountable outlet microfilter.

As shown in FIG. 1, the present invention is a personally portable vacuum desiccator 10 comprises a trap 12, a vacuum pump member operable to provide a source of low vacuum pressure, an electric motive or drive means 36 for operating the vacuum pump member, and an electrical control circuit, including an electrical power source. The control circuit is electrically connected to the electric motive means to control its operation, i.e., to turn it on and off. The trap 12 includes a desiccator cartridge 14 The desiccator cartridge 14 has an interior chamber 16 containing a trapping agent 54 (see FIG. 2). Additionally, the desiccator cartridge 14 has an inlet port 18 and an outlet port 20 in gas/liquid communication with the interior chamber 16 of the cartridge 14. A vacuum pump head or member 22 serves as a source for a low pressure vacuum of about 250 mm Hg or less. The vacuum pump member 22 is placed after desiccant chamber 14 in the gas/liquid flow pathway to facilitate preventing fluid from entering the vacuum pump member. The vacuum pump head 22 has a low pressure port 24 and an exhaust port 26. The low pressure port 22 is in gas/liquid flow communication with the outlet port 20 of the desiccator cartridge 14. The exhaust port 26 of the vacuum pump head 22 is vented to atmosphere. When operated, the vacuum pump member 22 provides a low vacuum pressure to the interior chamber 16 of the desiccator cartridge. As further shown in FIG. 1., an electric motive means 36 is in communication with the vacuum pump member 22 via a coupling 38. The electric motive means 36 is a low voltage electric motor, which is operable to drive the vacuum pump member 22, thus providing a low vacuum pressure at the pump member's low pressure port 24. The electrical control circuit 40, including an electrical power source 46, is in electrical communication with the electric motive means 36 via an electric motor lead 42. The control circuit 40 controls the operation of the electric motive means.

Optionally, a delivery tube 32 is included with the desiccator device 10 to put the trap 14 in gas/liquid flow communication with a location to which a low negative vacuum pressure is to be applied, such as a wound site covered by an occlusive dressing (not shown). The delivery tube 32 consists of a single passage gas/liquid flow path, having an input end 33 and an output end 24, the output end 34 being connected to the inlet port 18 of the desiccator cartridge 14.

The components of the personally portable vacuum desiccator 10 can further comprise a housing 50 for containing or mounting the component parts of the vacuum desiccator 10. As exemplified in FIG. 1, the housing 50 contains the electric motive means 26 and the electrical control circuit 40. Alternatively, the housing 50 can contain the electric motive means 36, the electrical control circuit 40 and additionally, the desiccator cartridge 14 and/or the vacuum pump member 22.

The trap 12 comprises a desiccator cartridge 14. As shown in FIGS. 2A and 2B, the desiccator cartridge 14 encloses an interior space or chamber 16. The desiccator cartridge 14 is of a design and material construction to withstand the application of an appropriate vacuum without substantial collapse of the interior chamber 16. Some distortion of the cartridge while under vacuum is desirable in some applications, e.g., where buffering of the vacuum pressure of the system is beneficial or distortion of the chamber 16 is used as an index of the vacuum pressure within the interior chamber 16.

A trapping agent 54 is contained within the interior chamber 16 to retain (trap) fluids and moisture that enter the chamber 16. There are a variety of compositions available in the art that are appropriate trapping agents for practice in the present invention. A specific composition or combination of compositions useful as the trapping agent 54 is readily selectable by one of ordinary skill in the art in view of the teaching herein and in consideration of the characteristics of the fluid to be trapped. Examples of classes of such compositions suitable as trapping agents 54 include desiccants, adsorbents, absorbents and the combination of any of these. Specific examples include silica gel, sodium polyacrylate, potassium polyacrylamide and related compounds. Such moisture trapping materials are often found in disposable baby diapers and in feminine napkins. These compositions may be particulate trapping agents 54a or fibrous trapping agents 54b. In a preferred embodiment, the trapping agent 54 was a pillow-like structure (see FIG. 8), which included a fiber matrix material which served to contain and somewhat immobilize the other loose components of the trapping agent, and to act as a wick to distribute the fluid as it entered the interior chamber. The level of moisture in the interior chamber 16 proximate the outlet port 20 is monitored by a moisture sensor 84 (see FIG. 1). When the amount of moisture retained by the trapping agent 54 approaches saturation (as detected by the moisture sensor 84 or indicated by other means), the desiccator cartridge 14 may either be removed and disposed of or recharged with fresh desiccant material and repositioned in the device (depending on the design of the desiccator cartridge). Other means for detecting the degree of saturation of the trapping agent 54 are available. For example, the desiccant cartridge 14 may be constructed in part from a transparent material, allowing the trapping agent 54 to be directly observed. The degree of saturation of the trapping agent 54 maybe indicated by a color change in a component of the trapping agent 54 in response, for example, to a pH change or degree of hydration.

In a preferred embodiment of the vacuum desiccator 10, all of the components in gas/liquid flow communication are replaceable. This allows the components of the device that are exposed to contact with the wound fluids to be separable from the other components of the device to facilitate cleaning or disposal of contaminated components. In particular, the desiccator cartridge 14 is removable from the device 10 and separately disposable. A fresh desiccator cartridge 14 is installed in the desiccator 10 to replace the removed cartridge. Alternatively, the cartridge 14 can be constructed to make its interior chamber 16 accessible, e.g., through a lid or by disassembly, whereby the used trapping agent 54 can be replaced with fresh. The refreshed desiccator cartridge may then be reattached to vacuum desiccator 10. This feature may be useful where the desiccator cartridge and vacuum pump head are combined as a single integrated unit (see FIG. 4).

Figure 5A:
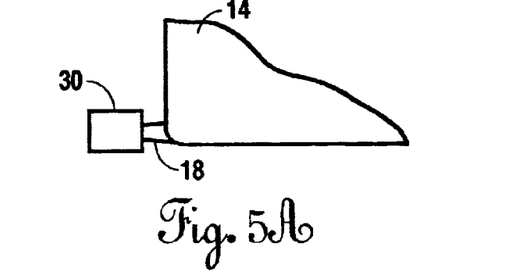
FIG. 5A is a partial top plan view of the inlet portion of the desiccator cartridge showing the inlet port with a one-way gas/fluid flow valve installed.
Figure 5B:
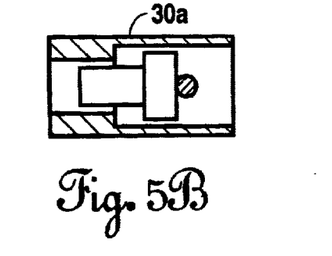
FIGS. 5B and 5C are partial cross-sectional views of two types of one-way gas/liquid flow valves.
Figure 5C:
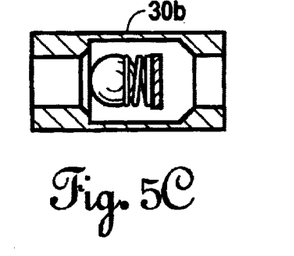

The desiccator cartridge 14 has a single, gas/liquid flow pathway, which is the inlet port 18, as the only inlet path into the trap 12. The flow path at the inlet port 18 is unidirectional, in that gas/liquid flow can enter the trap via the inlet port 18, but not exit or back flow out of the trap 14 via the inlet port 18. Unidirectional flow at the inlet port is accomplished by a one-way valve 30 located proximate the inlet port 18 of the desiccator cartridge 14 (see FIG. 5A). The one-way valve 30 prevents the contents of the desiccator cartridge 14 from back-flowing out of the inlet port 18. The one-way valve 30 maybe separable from the desiccator cartridge 14, as shown in FIG. 5A, or it may be incorporated into the cartridge 14 proximate the inlet port 18 (not shown). One-way gas/liquid flow valves practicable in the present invention are known in the art and selectable by the ordinary skilled artisan for use in the present invention. Examples of such one-way valves include biased and/or unbiased piston-type 30*a* and ball-stop 30*b* valves as exemplified in FIGS. 5B and 5C.

Figure 3:
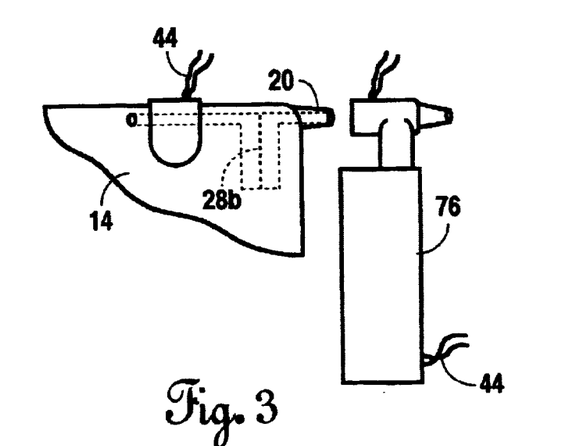
FIG. 3 is a partial top plan view of the outlet port portion of the desiccator cartridge showing in phantom a micro-filter integral to the desiccator cartridge flow path, and also a vacuum pressure sensor mountable to the outlet port of the cartridge.

A micro-filter 28 useful for blocking bacteria and/or untrapped moisture from passing into the vacuum pump member or from being vented to atmosphere is located in the gas/liquid flow path of the device 10 after the interior chamber 16 of the desiccator cartridge. The micro-filter 28 may be located proximate the outlet port 20 to protect the pump member 22 and/or proximate the exhaust port 26 to prevent venting bacteria (or moisture) to atmosphere. The micro-filter may be an in-line micro-filter 28*a* separate from the desiccator cartridge as shown in FIG. 2B, or an integral micro-filter 28*b* incorporated into the cartridge 14 proximate the outlet port 20 as shown in FIG. 3.

Figure 4:
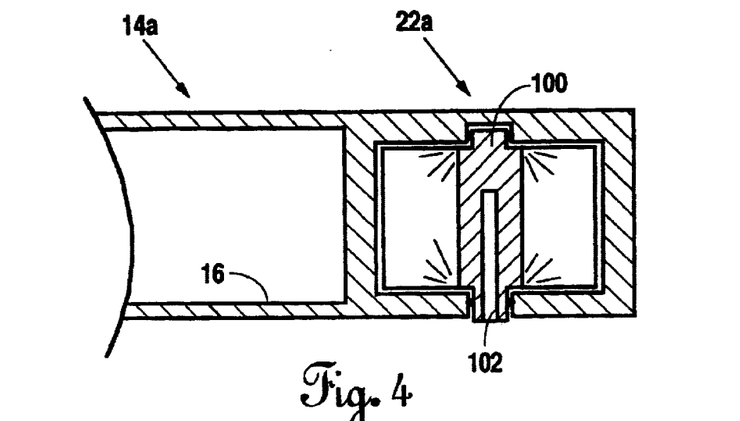
FIG. 4 is a cross-sectional view through a side elevation of a combination of a desiccator cartridge and vacuum pump head as an integral unit.

As shown in FIG. 1, an electric motive means 36 is coupled to the vacuum pump member 22 of the vacuum desiccator 10. In the preferred embodiment, the motive means 36 is an electric motor. Electric motors practicable in the present invention are known to and selectable by one of ordinary skill in the art in view of the teachings and figures contained herein. For example, a miniature, oil-less diaphragm pump is commercially available from the Gast Manufacturing, Inc. (Michigan): series 3D 1060, model 101-1028. The electric motor 36 communicates with the vacuum pump member 22 via a drive coupling 38 to drive the pump. The drive coupling 38 for connecting the motor 36 to the pump head 22 may be accomplished by any of a number of means known to and practicable by the ordinary skilled artisan. For example, a motor shaft coupling 38 maybe integrated with the vacuum pump head, i.e., the motor 36 and pump member 22 are substantially a single unit. Alternatively, a motor shaft coupling 38 may be mechanically coupled to the vacuum pump head 22 so as to be readily separable from the pump head 22. For instance, as exemplified in FIG. 4, the hub 100 of a rotary-vane pump head 22*a* has a motor shaft receiver 102 for accepting the end or spindle of a shaft coupling 38 of a motor 36. The shaft receiver 102 has a threaded, keyed or similar interfacing configuration (not shown) complementary to the spindle or end of the shaft coupling 38 of the motor 36. As a further alternative, the motor 36 maybe magnetically coupled (not shown) to the pump head 22 so as to again be readily separable from the vacuum pump member 22. A readily separable motive means 36 is particularly useful where the vacuum pump member 22 and the desiccator cartridge 14 are integrated together as a unit, as shown in FIG. 4.

Figure 6:
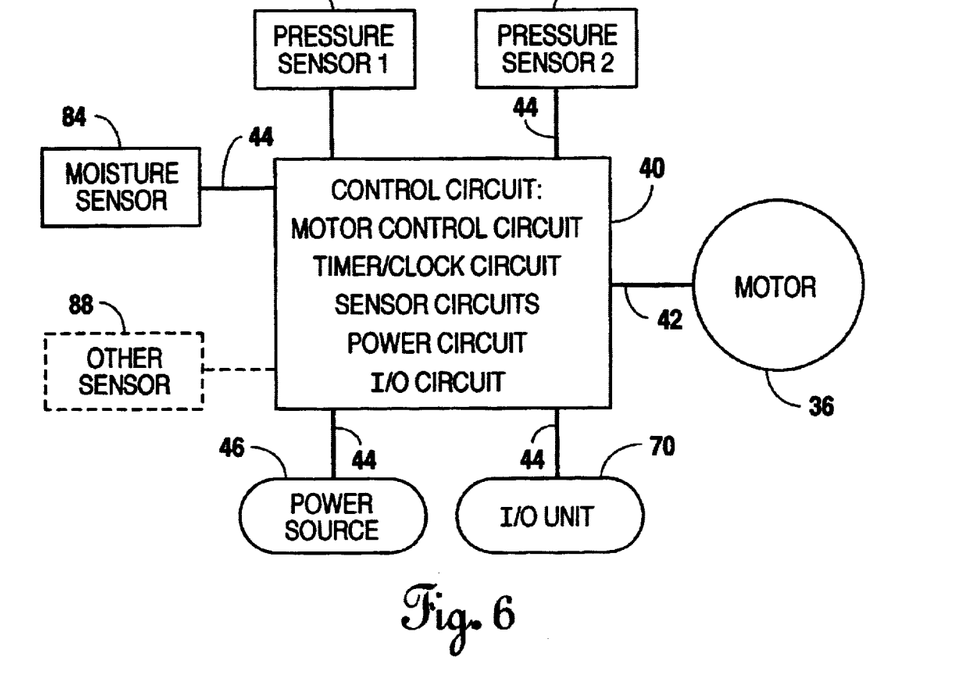
FIG. 6 is a block diagram of the electric control circuit of the desiccator device indicating its sub-circuits and the interconnect relationship with certain ancillary components.

As shown in FIG. 6, the present vacuum desiccator device 10 includes an electrical control circuit 40 that comprises logic and switching circuits and a number of ancillary circuits and functions, external sensors, electrical connections and a power source. In the preferred embodiment, the purpose of the electrical control circuit 40 is to monitor the condition of the device 10 and to control operation of the motive means 36. The ancillary circuits can be chosen for inclusion in an embodiment of the device 10 to affect one or more of the following functions: device data Input/Output, electrical power, sensor signal processing and motor control (power to the motor). An I/O unit 70 for accomplishing device data input and out put can include data input means such as a power and data entry switches (e.g., a key pad and/or on-off switch), and a readout display and alarms. Such I/O units 70 are well known in the art, and are readily practicable in the present invention by the ordinary skilled artisan. Other ancillary circuits and other sensors 88 may be provided at the user's option, and are similarly accomplishable by the ordinary skilled artisan.

Figure 7A:
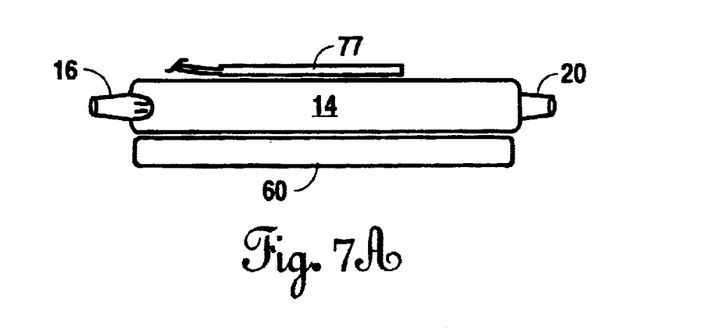
FIGS. 7A and 7B show alternative strain-gauge means for monitoring vacuum pressure in the interior chamber of the desiccator cartridge.
Figure 7B:
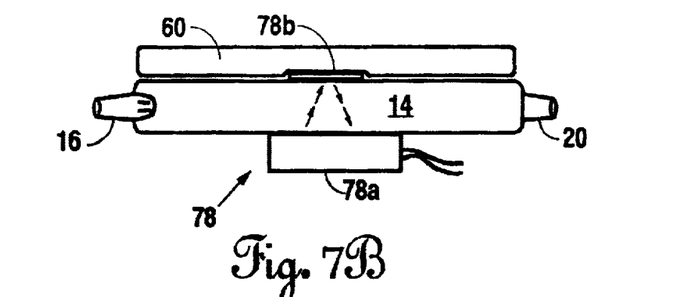

In the preferred embodiment exemplified in FIG. 1, the power source 46 for storing and providing electrical energy for the device 10 is a battery 60. In the preferred embodiment, the power source 46 is removable from the electrical control circuit 40 and is easily replaceable. The POLAROID® P100 Polapulse™battery is an example of an appropriate battery 60 useful as a power source 46 in the present vacuum desiccator device 10 in a preferred embodiment because of its planar configuration and low profile. See FIGS. 7A and 7B.

It is intended that the electrical control circuit have sensory capabilities to detect certain physical conditions of the device 10, and to utilize the conditions to control operation of the motor 36, and other appropriate functions of the control circuit 40. These ancillary sensory circuits include: a moisture sensor 84 and circuit, for detecting the presence of moisture proximate the outlet port 20 of the desiccant cartridge 14; at least one vacuum pressure sensor 76 and circuit, for detecting a vacuum pressure in the interior chamber or elsewhere in the device; and a pressure differential sensor circuit, for sensing a difference in pressure between two sections of the gas/liquid flow pathway of the device 10, e.g., between the inlet and outlet ports 18 & 20 of the desiccator cartridge 14. The sensors are interconnected to the control circuit 40 via electrical leads 44. Sensors appropriate for accomplishing the various sensory functions of an electrical control circuit are known in the art and are readily adaptable for practice in the present invention by the ordinary skilled artisan. For example, a vacuum pressure sensor 76 (MPL model 500, diaphragm-type pressure differential sensor) suitable for practice in the present device is commercially available from Micro Pneumatic Logic, Inc. (Florida) from a line of pressure sensors. Other types of sensors are adaptable for use in the present invention for detecting or sensing pressure, such as surface strain gauges mounted on the surface of the desiccator cartridge 14, and optical displacement gauges mounted to transmit light through the surfaces of desiccator cartridge 14. For example, an optical fiber strain gauge 77 is commercially available from FISO Technologies (Quebec, model FOS "C" or "N") from a line of optical strain gauges. This sensor can be used to monitor and indicate the presence of a vacuum in the desiccator cartridge by displacement (bending) of the cartridge surface under the force of a vacuum in the interior chamber 16. Optical displacement/strain gauges 78 are also commercially, including for the detection of fluid intrusion into a section of tubing. These gauges typically comprise a combination light source/detector 78a and a mirror 78b. Distortion of the surface of the desiccator cartridge 14 on which the mirror 78b is mounted alters the reflection path of the emitted light as it passes through the cartridge to return to the detector, which alteration is detectable. Of course, this requires the walls of the cartridge 14 proximate the optical displacement gauge 78 to be transparent to the light. The use of more than one pressure sensor 76 can allow sensing and/or measurement of the pressure differential between two different points in the gas/liquid flow pathway, such as between the inlet and outlet ports 18 & 20 of the desiccator cartridge 14.

The vacuum pressure sensor 76 is used to monitor the vacuum pressure in the interior chamber 16 of the desiccator cartridge 14. When the vacuum pressure detected in the chamber 16 by the pressure sensor 76 is sufficient, the electric control circuit 40 may switch off the motor 36, thereby conserving electrical power. When the vacuum pressure detected in the chamber 16 by the pressure sensor 76 is no longer sufficient the control circuit 40 may switch on the motor 36 to reestablish an appropriate vacuum pressure in the interior chamber 16 of the desiccator cartridge 14. Also, the electrical control circuit 40 can include a clock/timer circuit for intermittently operating the electric motive means 36, as another way of conserving electrical power. The I/O unit 70 can be utilized to set the time interval for the control circuit's intermittent operation of the motor 36.

In an alternative preferred embodiment of the vacuum desiccator 10, the battery 60 of the power source 46 is integral with the desiccator cartridge 14a. As exemplified in FIG. 8, the battery 60 is contained in a battery compartment 110, which is integral to the structure of the desiccator cartridge 14a. Battery leads 112 connect the battery 60 to electrical battery contacts 114 on the exterior surface 120 of the desiccator cartridge 14a. In this embodiment, the desiccator cartridge 14a and battery 60 are replaceable as a unit.

Figure 8:
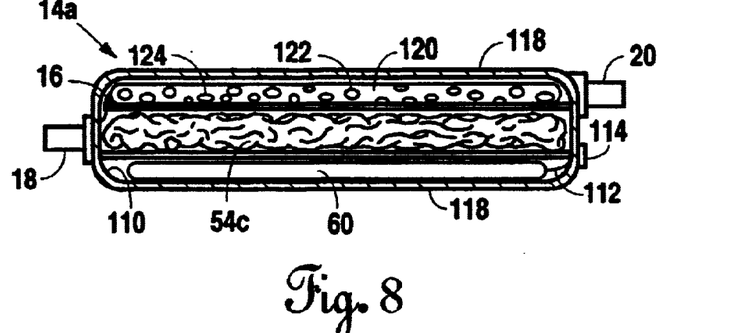
FIG. 8 is a partial cross-section of a side elevation of a desiccator cartridge showing the interior components and their layout.

FIG. 8 also illustrates another preferred feature of a desiccator cartridge 14, in which a gas flow channel is disposed inside the interior chamber 16 of the cartridge 14a. In the embodiment illustrated, the flow channel 120 is a tube connected to the outlet port 20 and having a length sufficient to allow it to be coiled or snaked about the interior chamber 16 (also see FIG. 9B). The flow channel tube 120 has perforations 122 along its length, or is otherwise constructed, to allow gas flow from the interior chamber 16 into the lumen of the flow channel tube 120 under the force of the vacuum pressure from the pump member 22. Further shown in FIG. 8, is trapping agent 54c having a pillow-like structure. The flow channel tube 120 is laid out on one side of the pillow trapping agent 54c. In the preferred embodiment, the pillow trapping agent 54c was constructed using 10 grams of sodium polyacrylate distributed between two layers of an elastic mesh material (nylon stocking). In addition to elastic mesh material, other fabrics are suitable for practice with the moisture trapping pillow 54c, including knitted fabric mesh materials like gauze and similar fabrics. To maintain even distribution of the sodium polyacrylate, the two layers of elastic mesh material were sewn together to form compartments. The volume of the interior chamber 16 of the desiccator cartridge 14 was sufficient to hold the pillow and about 50 cc of trapped moisture.

Figure 9A:
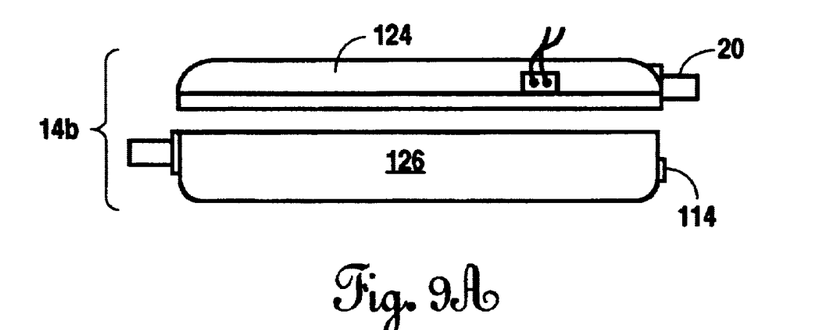
FIG. 9A is an exploded view of a side elevation of a desiccator cartridge showing a cover member incorporating an integral gas flow channel.
Figure 9B:
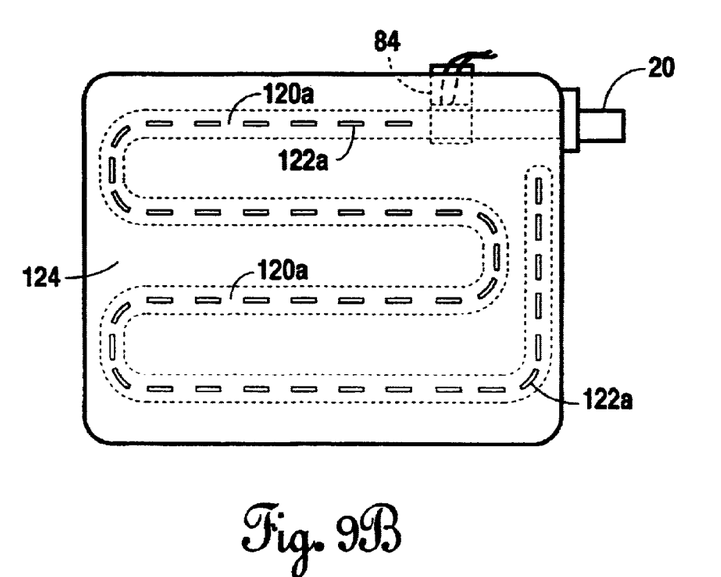
FIG. 9B is a bottom plan view of the cover member of FIG. 9A illustrating an example of an integral gas flow channel layout (in phantom) and the perforations by which the integral channel is in gas flow communication with the interior chamber of the desiccator cartridge.

A flow channel may be accomplished by means other than a tube. For example, a flow channel may be integrated into the desiccator cartridge 14 and be in gas flow communication with the interior chamber 16. This embodiment of a desiccator cartridge 14 can be accomplished as shown in FIGS. 9A and 9B, wherein the cartridge 14b has a cover member 124 and a body member 126 (FIG. 9A). The cartridge cover member 124 has a gas flow channel 120a integrated into it. The integral flow channel 120a has perforations 122a along its length, or is otherwise constructed, to allow gas flow from the interior chamber into the lumen of the integral channel 120a under the force of the vacuum pressure from the pump member 22.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A personally portable vacuum desiccator comprising:
    a moisture trap, the trap further comprising a desiccator cartridge having an interior chamber containing a trapping agent, and an inlet port and an outlet port in gas/liquid communication with the interior chamber;
    a vacuum pump member having a low pressure port and an exhaust port, the low pressure port in gas/liquid flow communication with the outlet port of the desiccator cartridge and with the exhaust port vented to atmosphere, and the vacuum pump member being operable to provide a low vacuum pressure to the interior chamber;
    an electric motive means in communication with the vacuum pump member and operative to drive the vacuum pump member; and
    an electrical control circuit, including an electrical power source, the control circuit in electrical communication with and operative to control operation of the electric motive means;
    wherein said personally portable vacuum desiccator is generally flat and may be worn unobtrusively by a user and is adaptable for collecting and trapping liquid from a wound or incision on the user in said moisture trap.

2. The personally portable vacuum desiccator of claim 1, further comprising a single passage gas/liquid flow path delivery tube, having an input end and an output end, the output end being connected to the inlet port of the desiccator cartridge.

3. The personally portable vacuum desiccator of claim 1, further comprising a housing containing the electric motive means and the electrical control circuit.

4. The personally portable vacuum desiccator of claim 1, further comprising a housing containing the electric motive means and the electrical control circuit and at least one additional element selected from the group consisting of the desiccator cartridge and the vacuum pump member.

5. The personally portable vacuum desiccator of claim 1, wherein the vacuum pump member is integral with the desiccator cartridge.

6. The personally portable vacuum desiccator of claim 1, wherein the electric motive means includes an electric motor mechanically coupled to the vacuum pump member.

7. The personally portable vacuum desiccator of claim 1, wherein the electric motive means includes an electric motor magnetically coupled to the vacuum pump member.

8. The personally portable vacuum desiccator of claim 1, wherein the electrical control circuit includes an electrical power source comprising a battery.

9. The personally portable vacuum desiccator of claim 1, wherein the electrical control circuit includes an electrical power source comprising a battery, and the battery is removable from the electrical control circuit and replaceable.

10. The personally portable vacuum desiccator of claim 1, further comprising a one-way valve disposed proximate the inlet port of the desiccator cartridge, the one-way valve preventing gas/liquid and particulate flow out of the inlet port.

11. The personally portable vacuum desiccator of claim 1, wherein the electrical control circuit includes a moisture sensor for detecting the presence of moisture proximate the low pressure port of the vacuum pump member.

12. The personally portable vacuum desiccator of claim 1, wherein the electrical control circuit includes a timer circuit for intermittently operating the electric motive means.

13. The personally portable vacuum desiccator of claim 1, wherein the electrical control circuit includes a vacuum pressure sensor for detecting a vacuum pressure in the interior chamber of the desiccator cartridge.

14. The personally portable vacuum desiccator of claim 1, wherein the electrical control circuit includes a pressure differential sensor for sensing a difference in pressure between the inlet and outlet ports of the desiccator cartridge.

15. The personally portable vacuum desiccator of claim 1, wherein the desiccator cartridge is removable from the vacuum desiccator and replaceable.

16. The personally portable vacuum desiccator of claim 1, wherein components in gas/liquid flow communication are replaceable.

17. The personally portable vacuum desiccator of claim 1, wherein the desiccator cartridge contains a trapping agent selected from the group consisting of: a desiccant, an adsorbent and an absorbent.

18. The personally portable vacuum desiccator of claim 1, further comprising a micro-filter positioned after the outlet port of the desiccator cartridge and before the exhaust port of the vacuum pump member, the micro-filter blocking the passage of bacteria.

19. The personally portable vacuum desiccator of claim 1, wherein the power source is integrally combined with the desiccator cartridge, and the combined desiccator-power source being installable in and removable from the vacuum desiccator as a single unit.

20. A personally portable vacuum desiccator comprising:
a desiccator cartridge, the cartridge being removable from the vacuum desiccator and replaceable, and having an interior chamber containing a trapping agent, the trapping agent being a moisture tapping pillow, and an inlet port and an outlet port in gas/liquid communication with the interior chamber, and a one-way valve disposed proximate the inlet port for preventing gas/liquid and particulate flow out of the inlet port;
a single passage gas/liquid flow pathway having an input end and an output end, the output end being connected to the inlet port of the desiccator cartridge;
a vacuum pump member having a low pressure port and an exhaust port, the low pressure port in gas/liquid flow communication with the outlet port of the desiccator cartridge and with the exhaust port vented to atmosphere, and the vacuum pump member being operable to provide a low vacuum pressure to the interior chamber;
an electric motive means in communication with the vacuum pump member and operative to drive the vacuum pump member, the electric motive means including an electric motor coupled to the vacuum pump member; and
an electrical control circuit, including an electrical power source, the control circuit in electrical communication with and operative to control operation of the electric motive means, the electrical power source comprising a battery, with the battery being removable from the electrical control circuit and replaceable, and wherein the electrical control circuit includes one or more ancillary circuits selected from the group consisting of: a power circuit for turning the electrical control circuit on and off, a moisture sensor for detecting the presence of moisture proximate the low pressure port of the vacuum pump member, a timer circuit for intermittently operating the electric motive means, a vacuum pressure sensor for detecting a vacuum pressure in the interior chamber of the desiccator cartridge, a pressure differential sensor for sensing a difference in pressure between the inlet and outlet ports of the desiccator cartridge.

21. A personally portable vacuum desiccator for draining and collecting excess fluid from a wound ox incision on a user, said vacuum desiccator comprising;
a thin moisture trap having a fluid trapping agent, an inlet port, and an outlet port;
a delivery tube having a first end positionable in gas/liquid flow communication with the wound or incision on the user and a second end in gas/liquid flow communication with said inlet port;
a vacuum pump in gas/liquid flow communication with said outlet port;
an electric motor operably connected to said vacuum pump; and
a control circuit in electrical communication with said motor, said control circuit having an electric power source and being operable for controlling the operation of said motor;
said vacuum desiccator being transportable upon the user's person
said vacuum pump being operable to draw fluid from the wound or incision through said delivery tube and into said moisture trap;

said fluid trapping agent having a capacity for trapping a volume of the fluid.

22. The personally portable vacuum desiccator of claim 21 wherein said delivery tube comprises a single passage gas/liquid flow path.

23. The personally portable vacuum desiccator of claim 21 wherein:

said moisture trap comprises a desiccator cartridge having an interior chamber;

said interior chamber having a gas flow channel and said fluid trapping agent disposed therein;

said gas flow channel being connected to said outlet port.

24. The personally portable vacuum desiccator of claim 23 wherein said gas flow channel comprises a second tube having perforations therein.

25. The personally portable vacuum desiccator of claim 24 wherein said second rube is arranged in a configuration selected from the group consisting of coiled and snaked.

26. The personally portable vacuum desiccator of claim 23 wherein said desiccator cartridge comprises a cover member and a body member, said gas flow channel being integrated into said cover member.

27. The personally portable vacuum desiccator of claim 21 further comprising a one-way valve proximate said inlet port to prevent gas/liquid flow out of said moisture trap through said inlet port.

28. The personally portable vacuum desiccator of claim 21 further comprising a micro-filter proximate said outlet port to prevent bacteria or moisture from leaving said moisture tap through said outlet port.

29. The personally portable vacuum desiccator of claim 21 further comprising a moisture sensor proximate said outlet port and in communication wit said control for controlling said motor in response to the detection of moisture proximate circuit said outlet port.

30. The personally portable vacuum desiccator of claim 21 further comprising a vacuum pressure sensor for detecting the vacuum pressure within said moisture trap, said vacuum pressure sensor being in communication with said control circuit for controlling said motor in response to said vacuum pressure.

31. The personally portable vacuum desiccator of claim 21 further comprising a pressure differential sensor for detecting the pressure differential between said inlet port and said outlet port, said pressure differential sensor being in communication with said control circuit for controlling said motor in response to said pressure differential.

32. The personally portable vacuum desiccator of claim 21 wherein said volume is about 50 cc.

33. The personally portable vacuum desiccator of claim 21 wherein said fluid tapping agent is selected from the group consisting of desiccants, adsorbent; and absorbents.

34. The personally portable vacuum desiccator of claim 21 wherein said moisture trap has a generally rectangular shape.

* * * * *

UNITED STATES PATENT AND TRADEMARK OFFICE
CERTIFICATE OF CORRECTION

PATENT NO. : 6,648,862 B2
DATED : November 18, 2003
INVENTOR(S) : Richard Watson It is certified that error appears in the above-identified patent and that said Letters Patent is hereby corrected as shown below:

Column 1,
Line 7, the word "p-umps" should be -- pumps --;
Line 34, "U.S. Pat. No. 6,024,7311", should be -- U.S. Pat. No. 6,024,731 --;

Column 12,
Line 46, the word "ox" should be -- or --;
Line 64, after the word "person" a semicolon -- ; -- should be inserted;

Column 13,
Line 17, the word "rube" should be -- tube --;

Column 14,
Line 2, the word "tap" should be -- trap --;
Line 5, the word -- circuit -- should be inserted after the word "control";
Line 8, the word "circuit" should be deleted in the last line; and
Line 23, the word "tapping" should be -- trapping --; the word "adsorbent" should be -- adsorbents --; the semicolon should be a comma.

Signed and Sealed this

Tenth Day of August, 2004

JON W. DUDAS
*Acting Director of the United States Patent and Trademark Office*